US006284512B1

(12) United States Patent
Jones et al.

(10) Patent No.: US 6,284,512 B1
(45) Date of Patent: Sep. 4, 2001

(54) CHEMICALLY MODIFIED MUTANT ENZYMES AND METHODS FOR PRODUCING THEM, AND SCREENING THEM FOR AMIDASE AND/OR ESTERASE ACTIVITY

(75) Inventors: J. Bryan Jones, 1275 Seaforth Crescent, RR 3, Lakefield, Ontario (CA), K0L 2H0; Erika Plettner, Salt Lake City, UT (US)

(73) Assignees: Genencor International, Inc., Rochester, NY (US); J. Bryan Jones, Ontario (CA)

( * ) Notice: Subject to any disclaimer, the term of this patent is extended or adjusted under 35 U.S.C. 154(b) by 0 days.

(21) Appl. No.: 09/234,956

(22) Filed: Jan. 21, 1999

Related U.S. Application Data

(60) Provisional application No. 60/072,266, filed on Jan. 23, 1998.

(51) Int. Cl.$^7$ .................................................. C12N 9/54
(52) U.S. Cl. .......................... 435/221; 435/19; 435/183; 435/263; 435/113; 435/440; 435/124; 435/219; 435/220; 435/222; 424/94.64; 426/53; 510/220; 510/238; 510/236; 510/320; 510/392; 510/530
(58) Field of Search .............................. 435/19, 183, 263, 435/113, 440, 124, 219, 220, 221, 222; 510/226, 236, 320, 392, 530; 426/53

(56) References Cited

U.S. PATENT DOCUMENTS

| | | | |
|---|---|---|---|
| 5,208,158 | 5/1993 | Bech et al. ............................ | 435/219 |
| 5,244,791 | 9/1993 | Estell ................................... | 435/68.1 |
| 5,316,935 | 5/1994 | Arnold et al. ........................ | 435/222 |
| 5,316,941 | 5/1994 | Estell et al. ......................... | 435/252.3 |
| 5,403,737 | 4/1995 | Abrahmsen et al. ................. | 435/252.3 |
| 5,629,173 | 5/1997 | Abrahmsen et al. ................. | 435/68.1 |

FOREIGN PATENT DOCUMENTS

| | | |
|---|---|---|
| WO 91/16423 | 10/1991 | (WO) . |
| WO 96/27671 | 9/1996 | (WO) . |

OTHER PUBLICATIONS

Plettner et al., "A Combinatorial Approach to Chemical Modification of Subtilisin Bacillus ientus," *Bioorganic & Medicinal Chemistry Letters*, 8:2291–2296 (1998).
DeSantis et al., "Chemical Modifications at a Single Site Can Induce Significant Shifts in the pH Profiles of a Serine Protease," *J. Am Chem. Soc.*, 120:8582–8586 (1998).
DeSantis et al., "Site–Directed Mutagenesis Combined with Chemical Modification as a Strategy for Altering the Specificity of the S1 and S1' Pockets of Subtilisin *Bacillus Ientus*," *Biochemistry*, 37: 5968–5973 (1998).
Berglund et al., "Altering the Specificity of Subtilisin *B. lentus* by Combining Site–Directed Mutagensis and Chemical Modification," *Bioorganic & Medicinal Chemsitry Letters*, 6:2507–2512 (1996).

Bech et al., "Chemical Modifications of a Cysteinyl Residue Introduced in the Binding Site of Carboxypeptidase Y by Site–Directed Mutagenesis," *Carlsberg Res. Commun.*, 53:381–393 (1988).
Wynn et al., "Chemical Modification of Protein Thiols: Formation of Mixed Disulfides," *Methods in Enzymology*, 251:351–356 (1995).
Bonneau et al., Alteration of the Specificity of Subtilisin BPN' by Site Directed Mutagenesis in Its $S_1$ and $S_1$' Binding Sites, *J. Am. Chem. Soc.*, 113:1026–1030 (1991).
Gloss et al., "Examining the Structural and Chemical Flexibility of the Active Site Base, Lys–258, of *Escherichia coli* Aspartate Aminotransferase by Replacement with Unnatural Amino Acids," *Biochemistry*, 34:12323–12332 (1995).
Wynne et al., "Mobile Unnatural Amino Acid Side Chains in the Core of Staphylococcal Nuclease," *Protein Science*, 5:1026–1031 (1996).
Berglund et al., "Chemical Modification of Cysteine Mutants of Subtilisin *Bacillus lentus* Can Create Better Catalysts Than The Wild–Type Enzyme," *J. Am. Chem. Soc.*, 119:5265–5266 (1997).
Gron et al., "A Highly Active and Oxidation–Resistant Subtilisin–Like Enzyme Produced by a Combination of Site–Directed Mutagenesis and Chemical Modification," *Euro. J. Biochem.*, 194:897–901 (1990).
Bech et al., "Significance of Hydrophobic $S_4$–$P_4$ Interactions in Subtilisin 309 from *Bacillus lentus*," *Biochemistry*, 32:2847–2852 (1993).
Wynn et al., "Unnatural Amino Acid Packing Mutants of *Escherichia coli* Thioredoxin Produced by Combined Mutagenesis/Chemical Modification Techniques," *Protein Science*, 2:395–403 (1993).

(List continued on next page.)

*Primary Examiner*—Rebecca E. Prouty
*Assistant Examiner*—Richard Hutson
(74) *Attorney, Agent, or Firm*—McCutchen, Doyle, Brown & Enersen, LLP (57) ABSTRACT

The present invention relates to a method for screening chemically modified mutant enzymes for amidase and/or esterase activity. This method includes providing a chemically modified mutant enzyme with one or more amino acid residues from an enzyme being replaced by cysteine residues, where at least some of the cysteine residues are modified by replacing thiol hydrogen in the cysteine residues with a thiol side chain, contacting the chemically modified mutant enzyme with a substrate for an amidase and/or a substrate for an esterase, and determining whether the chemically modified mutant enzyme exhibits amidase and/or esterase activity. The present invention also relates to chemically modified mutant enzymes and a method of producing them where one or more amino acid residues from an enzyme are replaced by cysteine residues, and the cysteine residues are modified by replacing at least some of the thiol hydrogen in the cysteine residue with a thiol side chain to form the chemically modified mutant enzyme. The thiol side chain is selected from the group consisting of $-SCH_2(p-CH_3-C_6H_4)$, $-SCH_2(p-OCH_3-C_6H_4)$, $-SCH_2(p-CF_3-C_6H_4)$, and $-SCH_2(2,4-diNO_2-C_6H_3)$.

10 Claims, 4 Drawing Sheets

OTHER PUBLICATIONS

Wynn et al., "Comparison of Straight Chain and Cyclic Unnatural Amino Acids Embedded in the Core of Staphylococcal Nuclease," *Protein Science*, 6:1621–1626 (1997).

Kawase et al., "Effect of Chemical Modification of Tyrosine Residues on Activities of Bacterial Lipase," *Journal of Fermentation and Bioengineering*, 72:317–319 (1991).

Raia et al., "Activation of *Sulfolobus solfataricus* Alcohol Dehydrogenase by Modification of Cysteine Residue 38 with Iodoacetic Acid," *Biochemistry*, 35:638–647 (1996).

Ramachandran et al., "Stabilization of Barstar by Chemical Modification of the Buried Cysteines," *Biochemistry*, 35:8776–8785 (1996).

Davies et al., "A Semisynthetic Metalloenzyme Based on a Protein Cavity That Catalyzes the Enantiosleective Hydrolysis of Ester and Amide Substrates," *J. Am. Chem. Soc.*, 119:11643–11652 (1997).

Polgar et al., "A New Enzyme Containing a Synthetically Formed Active Site. Thiol–Subtilisin," *Journal of American Chemical Society*, 88:3153–3154 (1966).

Stewart et al., "Catalytic Oxidation of Dithiols by a Semisynthetic Enzyme," *J. Am. Chem. Soc.*, 108:3480–3483 (1986).

Radziejewski et al., "Catalysis of N–Alkyl–1,4–Dihydronicotinamide Oxidation by a Flavopapain: Rapid Reaction in All Catalytic Steps," *J. Am. Chem. Soc.*, 107:3352–3354 (1985).

Hilvert et al., "A Highly Active Thermophilic Semisynthetic Flavoenzyme," *J. Am. Chem. Soc.*, 110:682–689 (1988).

Hilvert et al., "New Semisynthetic Flavoenzymes Based on a Tetrameric Protein Template, Glyceraldehyde–3–Phosphate Dehydrogenase," *J. Am. Chem. Soc.*, 107:5805–5806 (1985).

Rokita et al., "Synthesis and Characterization of a New Semisynthetic Enzyme, Flavolysozyme," *J. Am. Chem. Soc.*, 108:4984–4987 (1986).

Kokubo et al., "Flavohemoglobin: A Semisynthetic Hydroxylase Acting in the Absence of Reductase," *J. Am. Chem. Soc.*, 109:606–607 (1987).

Suckling et al., "Carbon–Carbon Bond Formation Mediated by Papain Chemically Modified by Thiazolium Salts," *Bioorganic & Medicinal Chemistry Letters*, 3:531–534 (1993).

Di Bello, "Total Synthesis of Proteins by Chemical Methods: The Horse Heart Cytochrome C Example," *Gazzetta Chimica Italiana*, 126:189–197 (1996).

O'Connor et al., "Probing an Acyl Enzyme of Selenosubtilisin by Raman Spectroscopy," *J. Am. Chem. Soc.*, 118: 239–240 (1996).

Peterson et al., "Nonessential Active Site Residues Modulate Slenosubtilisin's Kinetic Mechanism," *Biochemistry*, 34: 6616–6620 (1995).

Bell et al., "Kinetic Studies on the Peroxidase Activity of Selenosubtilisin," *Biochemistry*, 32:3754–3762 (1993).

Peterson et al., "Selenosubtilisin's Peroxidase Activity Does Not Require an Intact Oxyanion Hole," *Tetrahedron*, 53:12311–12317 (1997).

Wu et al., "Conversion of a Protease into an Acyl Transferase: Selenolsubtilisin," *J. Am. Chem. Soc.*, 111:4514–4515 (1989).

House et al., "$^1$H NMR Spectroscopic Studies of Selenosubtilisin," *Biochemistry*, 32:3468–3473 (1993).

Valenzuela et al., "Kinetic Properties of Succinylated and Ethylenediamine–Amidated δ–Chymotrypsins," *Biochim. Biophys. Acta*, 250:538–548 (1971).

Siddiqui et al., "Arthrobacter D–Xylose Isomerase: Chemical Modification of Carboxy Groups and Protein Engineering Of pH Optimum," *Biochem. J.*, 295:685–691 (1993).

Kuang et al., "Enantioselective Reductive Amination of αKato Acids to α–Amino Acids by a Pyridoxamine Cofactor in A Protein Cavity," *J. Am. Chem. Soc.*, 118:10702–10706 (1996).

West et al., "Enzymes as Synthetic Catalysts: Mechanistic and Active–Site Considerations of Natural and Modified Chymotrypsin," *J. Am. Chem. Soc.*, 112:5313–5320 (1990).

White et al., "Sequential Site–Directed Mutagenesis and Chemical Modification to Convert the Active Site Arginine 292 Of Aspartate Aminotransferase to Homoarginine," *Journal of the American Chemical Society*, 114:292–293 (1992).

Engler et al., "Critical Functional Requirement for the Guanidinium Group of the Arginine 41 Side Chain of Human Epidermal Growth Factor as Revealed by Mutagenic Inactivation and Chemical Reactivation," *The Journal of Biological Chemistry*, 267:2274–2281 (1992).

Planas et al., "Reengineering the Catalytic Lysine of Aspartate Aminotransferase by Chemical Elaboration of a Genetically Introduced Cysteine," *Biochemistry*, 30:8268–8276 (1991).

Smith et al., "An Engineered Change in Substrate Specificity of Ribulosebisphosphate Carboxylase/Oxygenase," *The Journal of Biological Chemistry*, 265:1243–1245 (1990).

Smith et al., "Subtle Alteration of the Active Site of Ribulose Bisphosphate Carboxylase/Oxygenase by Concerted Site–Directed Mutagenesis and Chemical Modification," *Biochemical and Biophysical Research Communications*, 152:579–584 (1988).

Smith et al., "Restoration of Activity to Catalytically Deficient Mutants of Ribulosebisphosphate Carboxylase/Oxygenase by Aminoethylation," *The Journal of Biological Chemistry*, 263:4921–4925 (1988).

Kanaya et al., "Role of Cysteine Residues in Ribonuclease H from *Escherichia coli*," *Biochem. J.*, 271:59–66 (1990).

Xu et al., "Amino Acids Lining the Channel of the γ–Aminobutyric Acid Type A Receptor Identified by Cysteine Substitution," *The Journal of Biological Chemistry*, 268:21505–21508 (1993).

Svensson et al., "Mapping the Folding Intermediate of Human Carbonic Anhydrase II. Probing Substructure by Chemical Reactivity and Spin and Fluorescence Labeling of Engineered Cysteine Residues," *Biochemistry*, 34:8606–8620 (1995).

Akabas et al., "Acetylcholine Receptor Channel Structure Probed in Cysteine–Substitution Mutants," *Science*, 258: 307–310 (1992).

Liu et al., "Site–Directed Fluorescence Labeling of P–Glycoprotein on Cysteine Residues in the Nucleotide Binding Domains," *Biochemistry*, 35:11865–11873 (1996).

Frillingos et al., "Cysteine–Scanning Mutagenesis of Helix II and Flanking Hydrophilic Domains in the Lactose Permease of *Escherichia coli*, " *Biochemistry*, 36:269–273 (1997).

Kirley, "Reduction and Fluorescent Labeling of Cyst(e)ine–Containing Proteins for Subsequent Structural Analyses," *Analytical Biochemistry*, 180:231–236 (1989).

Buckwalter et al., "Improvement in the Solution Stability of Porcine Somatotropin by Chemical Modification of Cysteine Residues," *J. Agric. Food Chem.*, 40:356–362 (1992).

Nishimura et al., "Reversible Modification of the Sulfhydryl Groups of *Escherichia coli* Succinic Thiokinase with Methanethiolating Reagents, 5,5'–Dithio–bis(2–Nitrobenzoic Acid), p–Hydroxymercuribenzoate, and Ethylmercurithiosalicylate," *Archives of Biochemistry and Biophysics*, 170:461–467 (1975).

Lewis et al., "Determination of Interactive Thiol Ionizations in Bovine Serum Albumin, Glutathione, and Other Thiols by Potentiometric Difference Titration," *Biochemistry*, 19:6129–6137 (1980).

Worku et al., "Identification of Histidyl and Cysteinyl Residues Essential for Catalysis by 5'–Nucleotidase," *FEBS Letters*, 167:235–240 (1984).

Smith et al., "Chemical Modification of Active Site Residues in γ–Glutamyl Transpeptidase," *The Journal of Biological Chemistry*, 270:12476–12480 (1995).

Smith et al., "Nonessentiality of the Active Sulfhydryl Group of Rabbit Muscle Creatine Kinase," *The Journal of Biological Chemistry*, 249:3317–3318 (1974).

Roberts et al., "Reactivity of Small Thiolate Anions and Cysteine–25 in Papain Toward Methyl Methanethiosulfonate," *Biochemistry*, 25:5595–5601 (1986).

Pardo et al., "Cysteine 532 and Cysteine 545 Are theN–Ethylmaleimide–Reactive Residues of the *Neurospora* Plasma Membrane $H^+$–ATPase," *The Journal of Biological Chemistry*, 264:9373–9379 (1989).

Hempel et al., "Selective Chemical Modification of Human Liver Aldehyde Dehydrogenases $E_1$ and $E_2$ by Iodoacetamide," *The Journal of Biological Chemistry*, 256:10889–10896 (1981).

Daly et al., "Formation of Mixed Disulfide Adducts at Cysteine–281 of the Lactose Repressor Protein Affects Operator And Inducer Binding Parameters," *Biochemistry*, 25:5468–5474 (1986).

Bodwell et al., "Sulfhydryl–Modifying Reagents Reversibly Inhibit Binding of Glucocorticoid–Receptor Complexes to DNA–Cellulose," *Biochemistry*, 23:1392–1398 (1984).

Alvear et al., "Inactivation of Chicken Liver Mevalonate 5–Diphosphate Decarboxylase by Sulfhydryl–Directed Reagents: Evidence of a Functional Dithiol," *Biochimica et Biophysica Acta*, 994:7–11 (1989).

Miller et al., "Peroxide Modification of Monoalkylated Glutathione Reductase," *The Journal of Biological Chemistry*, 266:19342–19360 (1991).

Soper et al., "Effects of Substrates on the Selective Modification of the Cysteinyl Residues of D–Amino Acid Transaminase," *The Journal of Biological Chemistry*, 254:10901–10905 (1979).

Stauffer et al., "Electrostatic Potential of the Acetylcholine Binding Sites in the Nicotinic Receptor Probed by Reactions Of Binding–Site Cysteines with Charged Methanethiosulfonates," *Biochemistry*, 33:6840–6849 (1994).

Nakayama et al., "Chemical Modification of Cysteinyl, Lysyl and Histidyl Residues of Mouse Liver 17β–Hydroxysteroid Dehydrogenase," *Biochimica et Biophysica Acta*, 1120:144–150 (1992).

Huang et al., "Improving the Activity of Immobilized Subtilisin by Site–Specific Attachment to Surfaces," *Anal. Chem.*, 69:4601–4607 (1997).

Brocklehurst, "Specific Covalent Modification of Thiols: Applications in the Study of Enzymes and Other Biomolecules," *Int. J. Biochem.*, 10:259–274 (1979).

Bruice et al., "Novel Alkyl Alkanethiolsulfonate Sulfhydryl Reagents. Modification of Derivatives of L–Cysteine," *Journal of Protein Chemistry*, 1:47–58 (1982).

Smith et al., "Simple Alkanethiol Groups for Temporary Blocking of Sulfhydryl Groups of Enzymes," *Biochemistry*, 14:766–771 (1975).

Polgar, "Spectrophotometric Determination of Mercaptide Ion, an Activated Form of SH–Group in Thiol Enzymes," *FEBS Letters*, 38:187–190 (1974).

Konigsberg, "Reduction of Disulfide Bonds in Proteins with Dithiothreitol," *Methods in Enzymology*, 25:185–188 (1972).

Kenyon et al., "Novel Sulfhydryl Reagents," *Methods Enzymol.*, 47:407–430 (1977).

Kluger et al., "Amino Group Reactions of the Sulfhydryl Reagent Methyl Methanesulfonothioate. Inactivation of D–3–hydroxybutyrate Dehydrogenase and Reaction with Amines in Water," *Can. J. Biochem.*, 58:629–632 (1980).

Kaiser, "Catalytic Activity of Enzymes Altered at Their Active Sites," *Angew. Chem. Int. Ed. Engl.*, 27:913–922 (1988).

CHEMICALLY MODIFIED MUTANT ENZYMES AND METHODS FOR PRODUCING THEM, AND SCREENING THEM FOR AMIDASE AND/OR ESTERASE ACTIVITY

CROSS-REFERENCE TO RELATED APPLICATIONS

This application claims the benefit of U.S. Provisional Patent Application Ser. No. 60/072,266, filed Jan. 23, 1998, which is hereby incorporated by reference.

FIELD OF THE INVENTION

The present invention relates to chemically modified mutant enzymes and a method of producing them and a method of screening them for amidase and/or esterase activity.

BACKGROUND OF THE INVENTION

Modifying enzyme properties by site-directed mutagenesis has been limited to natural amino acid replacements, although molecular biological strategies for overcoming this restriction have recently been derived (Cornish et al., *Angew. Chem.*, Int. Ed. Engl., 34:621–633 (1995)). However, the latter procedures are difficult to apply in most laboratories. In contrast, controlled chemical modification of enzymes offers broad potential for facile and flexible modification of enzyme structure, thereby opening up extensive possibilities for controlled tailoring of enzyme specificity.

Changing enzyme properties by chemical modification has been explored previously, with the first report being in 1966 by the groups of Bender (Polgar et al., *J. Am. Chem. Soc.*, 88:3153–3514 (1966)) and Koshland (Neet et al., *Proc. Natl. Acad. Sci. USA*, 56:1606–1611 (1966)), who created a thiolsubtilisin by chemical transformation ($CH_2OH \rightarrow CH_2SH$) of the active site serine residue of subtilisin BPN' to cysteine. Interest in chemically produced artificial enzymes, including some with synthetic potential, was renewed by Wu (Wu et al., *J. Am. Chem. Soc.*, 111:4514–4515 (1989); Bell et al., *Biochemistry*, 32:3754–3762 (1993)) and Peterson (Peterson et al., *Biochemistry*, 34:6616–6620 (1995)), and, more recently, Suckling (Suckling et al., *Bioorg. Med. Chem. Lett.*, 3:531–534 (1993)).

Enzymes are now widely accepted as useful catalysts in organic synthesis. However, natural, wild-type, enzymes can never hope to accept all structures of synthetic chemical interest, nor always be transformed stereospecifically into the desired enantiomerically pure materials needed for synthesis. This potential limitation on the synthetic applicabilities of enzymes has been recognized, and some progress has been made in altering their specificities in a controlled manner using the site-directed and random mutagenesis techniques of protein engineering. However, modifying enzyme properties by protein engineering is limited to making natural amino acid replacements, and molecular biological methods devised to overcome this restriction are not readily amenable to routine application or large scale synthesis. The generation of new specificities or activities obtained by chemical modification of enzymes has intrigued chemists for many years and continues to do so.

U.S. Pat. No. 5,208,158 to Bech et al. ("Bech") describes chemically modified detergent enzymes wherein one or more methionines have been mutated into cysteines. The cysteines are subsequently modified in order to confer upon the enzyme improved stability towards oxidative agents. The claimed chemical modification is the replacement of the thiol hydrogen with $C_{1-6}$alkyl.

Although Bech has described altering the oxidative stability of an enzyme through mutagenesis and chemical modification, it would also be desirable to identify one or more enzymes with altered properties such as activity, nucleophile specificity, substrate specificity, stereoselectivity, thermal stability, pH activity profile, and surface binding properties for use in, for example, detergents or organic synthesis. In particular, enzymes, such as subtilisins, tailored for peptide synthesis would be desirable. Enzymes useful for peptide synthesis have high esterase and low amidase activities. Generally, subtilisins do not meet these requirements and the improvement of the esterase to amidase selectivities of subtilisins would be desirable as would a rapid identification of subtilisins with improved esterase to amidase selectivities. However, previous attempts to tailor enzymes for peptide synthesis by lowering amidase activity have generally resulted in dramatic decreases in both esterase and amidase activities. Previous strategies for lowering the amidase activity include the use of water-miscible organic solvents (Barbas et al., *J. Am. Chem. Soc.*, 110:5162–5166 (1988); Wong et al., *J. Am. Chem. Soc.*, 112:945–953 (1990); and Sears et al., *Biotechnol. Prog.*, 12:423–433 (1996)) and site-directed mutagenesis (Abrahamsen et al., *Biochemistry*, 30:4151–4159 (1991); Bonneau et al., *J. Am. Chem. Soc.*, 113:1026–1030 (1991); and Graycar et al., *Ann. N.Y. Acad. Sci.*, 67:71–79 (1992)). However, while the ratios of esterase-to-amidase activities were improved by these approaches, the absolute esterase activities were lowered concomitantly. Abrahamsen et al., *Biochemistry*, 30:4151–4159 (1991). Chemical modification techniques (Neet et al., *Proc. Nat. Acad. Sci.*, 56:1606 (1966); Polgar et al., *J. Am. Chem. Soc.*, 88:3153–3154 (1966); Wu et al., *J. Am. Chem. Soc.*, 111:4514–4515 (1989); and West et al., *J. Am. Chem. Soc.*, 112:5313–5320 (1990)), which permit the incorporation of unnatural amino acid moieties, have also been applied to improve esterase to amidase selectivity of subtilisins. For example, chemical conversion of the catalytic triad serine (Ser221) of subtilisin to cysteine (Neet et al., *Proc. Nat. Acad. Sci.*, 56:1606 (1966); Polgar et al., *J. Am. Chem. Soc.*, 88:3153–3154 (1966); and Nakatsuka et al., *J. Am. Chem. Soc.*, 109:3808–3810 (1987)) or to selenocysteine (Wu et al., *J. Am. Chem. Soc.*, 111:4514–4515 (1989)), and methylation of the catalytic triad histidine (His 57) of chymotrypsin (West et al., *J. Am. Chem. Soc.*, 112:5313–5320 (1990)) effected substantial improvement in esterase-to-amidase selectivities. Unfortunately however, these modifications were again accompanied by 50- to 1000-fold decreases in absolute esterase activity.

Further, previous attempts to identify enzymes with improved esterase to amidase selectivites have resulted in a slow process which requires large quantities of chemically modified mutant enzymes. In particular, the kinetic constants of fully characterized chemically modified mutant enzymes have been evaluated by the method of initial rates with a colorimetric assay. Amidase activity was followed by the release of p-nitroanilide from the tetrapeptide substrate succinylalanylalanylprolyphenylalanyl p-nitroanilide (sucAAPF-pNa). The analogous thiobenzyl ester substrate succinyl-alanine-alanine-proline-phenylalanine-thiobenzyl ester (sucAAPF-SBn) does not have a chromogenic leaving group, so detection of hydrolysis requires reaction of the thiobenzyl leaving group with 5,5'-dithiobis-2,2'-nitrobenzoate (DTNB, Ellman's reagent). However, the full characterization and kinetic evaluation of new chemically modified mutant enzymes by this method is very material and time-consuming.

The present invention is directed to overcoming these deficiencies.

SUMMARY OF THE INVENTION

The present invention relates to a method for screening chemically modified mutant enzymes for amidase and/or esterase activity. This method includes providing a chemically modified mutant enzyme with one or more amino acid residues from an enzyme being replaced by cysteine residues, where at least some of the cysteine residues are modified by replacing thiol hydrogen in the cysteine residues with a thiol side chain, contacting the chemically modified mutant enzyme with a substrate for an amidase and/or a substrate for an esterase, and determining whether the chemically modified mutant enzyme exhibits amidase and/or esterase activity.

Another aspect of the present invention relates to a chemically modified mutant enzyme with one or more amino acid residues from an enzyme being replaced by cysteine residues, where at least some of the cysteine residues are modified by replacing thiol hydrogen in the cysteine residue with a thiol side chain. The thiol side chain can be $-SCH_2(p-CH_3-C_6H_4)$, $-SCH_2(p-OCH_3-C_3C_6H_4)$, $-SCH_2(p-CF_3-C_6H_4)$, or $-SCH_2(2,4-diNO_2-C_6H_3)$.

The present invention also relates to a method of producing a chemically modified mutant enzyme. This method includes providing an enzyme wherein one or more amino acids have been replaced with cysteine residues and replacing thiol hydrogen in at least some of the cysteine residues with a thiol side chain to form the chemically modified mutant enzyme. The thiol side chain can be $-SCH_2(p-CH_3-C_6H_4)$, $-SCH_2(p-OCH_3-C_6H_4)$, $-SCH_2(p-CF_3-C_6H_4)$, or $-SCH_2(2,4-diNO_2-C_6H_3)$.

The method for screening chemically modified mutant enzymes for amidase and/or esterase activity of the present invention provides a rapid enzyme modification screen to explore new chemically modified mutant enzymes ("CMMs") without the need to prepare large quantities of the new CMMs and without the material and time-consuming nature of the full characterization and kinetic evaluation of new CMMs.

The chemically modified mutant enzymes of the present invention exhibit an increased esterase to amidase ratio as compared to wild-type enzymes and, therefore, more efficiently catalyze peptide synthesis. In addition, the chemically modified mutant enzymes of the present invention are useful in formulating various detergent compositions and in the preparation of animal feed.

DETAILED DESCRIPTION OF THE INVENTION

The present invention relates to a method for screening chemically modified mutant enzymes for amidase and/or esterase activity. This method includes providing a chemically modified mutant enzyme with one or more amino acid residues from an enzyme being replaced by cysteine residues, where at least some of the cysteine residues are modified by replacing thiol hydrogen in the cysteine residues with a thiol side chain, contacting the chemically modified mutant enzyme with a substrate for an amidase and/or a substrate for an esterase, and determining whether the chemically modified mutant enzyme exhibits amidase and/or esterase activity.

Preferably, the enzyme is a protease. More preferably, the enzyme is a Bacillus subtilisin. Subtilisins are alkaline serine proteases that are finding increasing use in biocatalysis, particularly in chiral resolution, regioselective acylation of polyfunctional compounds, peptide coupling, and glycopeptide synthesis. The latter two applications are of particular interest, because they provide an alternative to site-directed mutagenesis and chemical modification for introducing unnatural amino acids into proteins. Subtilisins can catalyze peptide bond formation starting from an ester substrate, by first forming an acyl enzyme intermediate which then reacts with a primary amine to form the peptide product. This application thus requires high esterase activity to promote acyl enzyme formation and then low amidase activity to minimize hydrolysis of the peptide bond of the desired product Generally, subtilisins do not meet these requirements and the identification of subtilisins with improved esterase to amidase selectivities is needed.

Also, preferably, the amino acids replaced in the enzyme by cysteines are selected from the group consisting of asparagine, leucine, or serine. More preferably, the amino acid to be replaced is located in a subsite of the enzyme, preferably, the $S_1$, $S_1'$, or $S_2$ subsites. Most preferably, the amino acids to be replaced are N62, L217, and S166 where the numbered position corresponds to naturally-occurring subtilisin from Bacillus amyloliquefaciens or to equivalent amino acid residues in other subtilisins, such as Bacillus lentus subtilisin.

In a particularly preferred embodiment, the enzyme is a Bacillus lentus subtilisin. In another particularly preferred embodiment, the amino acid to be replaced by cysteine is N62, L217, or S166 and the thiol side chain group is selected from the group consisting of:
- $-SCH_2C_6H_5$;
- $-SCH_2(p-CH_3-C_6H_4)$;
- $-SCH_2(p-OCH_3-C_6H_4)$;
- $-SCH_2(p-COOH-C_6H_4)$;
- $-SCH_2C_6F_5$;
- $-SCH_2(p-CF_3-C_6H_4)$; and
- $-SCH_2(2,4-diNO_2-C_6H_3)$.

Preferably, for esterase activity, the ratio of chemically modified mutant enzyme to substrate is from about 1 M:10 M to about 1 M:$10^8$ M. Most preferably, the ratio of chemically modified mutant enzyme to substrate is about 1 M:$10^3$ M.

Preferably, for amidase activity, the ratio of chemically modified mutant enzyme to substrate is from about 1 M:10 M to about 1 M:$10^{10}$ M. Most preferably, the ratio of chemically modified mutant enzyme to substrate is about 1 M:$6 \times 10^3$ M.

A "chemically modified mutant enzyme" is an enzyme that has been changed by replacing an amino acid residue such as asparagine, leucine, or serine with a cysteine residue and then replacing the thiol hydrogen of the cysteine with a thiol side chain (e.g., —$SCH_2C_6H_5$, —$SCH_2(p\text{-}CH_3\text{—}C_6H_4)$, —$SCH_2(p\text{-}OCH_3\text{—}C_6H_4)$, —$SCH_2(p\text{-}COOH\text{—}C_6H_4)$, —$SCH_2C_6F_5$, —$SCH_2(p\text{-}CF_3\text{—}C_6H_4)$, and —$SCH_2(2,4\text{-}diNO_2\text{—}C_6H_3)$). After modification, the properties of the enzyme, i.e., activity or substrate specificity, may be altered. Preferably, the activity of the enzyme is increased.

The term "enzyme" includes proteins that are capable of catalyzing chemical changes in other substances without being changed themselves. The enzymes can be wild-type enzymes or variant enzymes. Enzymes within the scope of the present invention include pullulanases, proteases, cellulases, amylases, isomerases, lipases, oxidases, and reductases. The enzyme can be a wild-type or mutant protease. Wild-type proteases can be isolated from, for example, *Bacillus lentus* or *Bacillus amyloliquefaciens* (also referred to as BPN'). Mutant proteases can be made according to the teachings of, for example, PCT Publication Nos. WO 95/10615 and WO 91/06637, which are hereby incorporated by reference.

Several types of moieties can be used to replace the thiol hydrogen of the cysteine residue. These include —$SCH_2C_6H_5$, —$SCH_2(p\text{-}CH_3\text{—}C_6H_4)$, —$SCH_2(p\text{-}OCH_3C_6H_4)$, —$SCH_2(p\text{-}COOH\text{—}C_6H_4)$, —$SCH_2C_6F_5$, —$SCH_2(p\text{-}CF_3\text{—}C_6H_4)$, and —$SCH_2(2,4\text{-}diNO_2C_6H_3)$.

The terms "thiol side chain group," "thiol containing group," and "thiol side chain" are terms which are used interchangeably and include groups that are used to replace the thiol hydrogen of a cysteine used to replace one of the amino acids in an enzyme. Commonly, the thiol side chain group includes a sulfur through which the thiol side chain groups defined above are attached to the thiol sulfur of the cysteine.

The binding site of an enzyme consists of a series of subsites across the surface of the enzyme. The substrate residues that correspond to the subsites are labeled P and the subsites are labeled S. By convention, the subsites are labeled $S_1$, $S_2$, $S_3$, $S_4$, $S_1'$ and $S_2'$. A discussion of subsites can be found in Siezen et al., *Protein Engineering*, 4:719–737 (1991) and Fersht, *Enzyme Structure and Mechanism*, 2 ed., Freeman: N.Y. 29–30 (1985), which are hereby incorporated by reference. The preferred subsites are $S_1$, $S_2'$ and $S_2$.

Another aspect of the present invention relates to chemically modified mutant enzymes with one or more amino acid residues from an enzyme being replaced by cysteine residues, where at least some of the cysteine residues are modified by replacing thiol hydrogen in the cysteine residue with a thiol side chain to form a chemically modified mutant enzyme. The thiol side chain can be —$SCH_2(p\text{-}CH_3\text{—}C_6H_4)$, —$SCH_2(p\text{-}OCH_3\text{—}C_6H_4)$, —$SCH_2(p\text{-}CF_3\text{—}C_6H_4)$, or —$SCH_2(2,4\text{-}diNO_2\text{—}C_6H_3)$.

The present invention also relates to a method of producing a chemically modified mutant enzyme. This method involves providing an enzyme wherein one or more amino acids have been replaced with cysteine residues and replacing thiol hydrogen in at least some of the cysteine residues with a thiol side chain to form the chemically modified mutant enzyme. The thiol side chain can be —$CH_2(p\text{-}CH_3\text{—}C_6H_4)$, —$SCH_2(p\text{-}OCH_3\text{—}C_6H_4)$, —$SCH_2(p\text{-}CF_3\text{—}C_6H_4)$, or —$SCH_2(2,4\text{-}diNO_2\text{—}C_6H_3)$.

The amino acid residues of the present invention can be replaced with cysteine residues using site-directed mutagenesis methods or other methods well known in the art. See, for example, PCT Publication No. WO 95/10615, which is hereby incorporated by reference. One method of modifying the thiol hydrogen of the cysteine residue is set forth in the Examples.

The modified enzymes of the present invention can be formulated into known powdered and liquid detergents having a pH between 6.5 and 12.0 at levels of about 0.01 to about 5% (preferably 0.1% to 0.5%) by weight. These detergent cleaning compositions or additives can also include other enzymes, such as known proteases, amylases, cellulases, lipases, or endoglycosidases, as well as builders and stabilizers.

The modified enzymes of the present invention, especially subtilisins, are useful in formulating various detergent compositions. A number of known compounds are suitable surfactants useful in compositions comprising the modified enzymes of the present invention. These include nonionic, anionic, cationic, anionic, or zwitterionic detergents, as disclosed in U.S. Pat. No. 4,404,128 to Anderson and U.S. Pat. No. 4,261,868 to Flora et al., which are hereby incorporated by reference. A suitable detergent formulation is that described in Example 7 of U.S. Pat. No. 5,204,015 to Caldwell et al., which is hereby incorporated by reference. The art is familiar with the different formulations which can be used as cleaning compositions. In addition to typical cleaning compositions, it is readily understood that the modified enzymes of the present invention may be used for any purpose that native or wild-type enzymes are used. Thus, these modified enzymes can be used, for example, in bar or liquid soap applications, dishcare formulations, contact lens cleaning solutions or products, peptide synthesis, feed applications such as feed additives or preparation of feed additives, waste treatment, textile applications such as the treatment of fabrics, and as fusion-cleavage enzymes in protein production. The modified enzymes of the present invention may comprise improved wash performance in a detergent composition (as compared to the precursor). As used herein, improved wash performance in a detergent is defined as increasing cleaning of certain enzyme-sensitive stains such as grass or blood, as determined by light reflectance evaluation after a standard wash cycle.

The addition of the modified enzymes of the present invention to conventional cleaning compositions does not create any special use limitation. In other words, any temperature and pH suitable for the detergent is also suitable for the present compositions as long as the pH is within the above range and the temperature is below the described modified enzyme's denaturing temperature. In addition, modified enzymes in accordance with the invention can be used in a cleaning composition without detergents, again either alone or in combination with builders and stabilizers.

In another aspect of the present invention, the modified enzymes are used in the preparation of an animal feed, for example, a cereal-based feed. The cereal can be at least one of wheat, barley, maize, sorghum, rye, oats, triticale, and rice. Although the cereal component of a cereal-based feed constitutes a source of protein, it is usually necessary to include sources of supplementary protein in the feed such as those derived from fish-meal, meat-meat, or vegetables. Sources of vegetable proteins include at least one of full fat soybeans, rapeseeds, canola, soybean-meal, rapeseed-meal, and canola-meal.

The inclusion of a modified enzyme of the present invention in an animal feed can enable the crude protein value and/or digestibility and/or amino acid content and/or digestibility coefficients of the feed to be increased. This permits a reduction in the amounts of alternative protein sources and/or amino acids supplements which had previously been necessary ingredients of animal feeds.

The feed provided by the present invention may also include other enzyme supplements such as one or more of β-glucanase, glucoamylase, mannanase, α-galactosidase, phytase, lipase, a-arabinofuranosidase, xylanase, a-amylase, esterase, oxidase, oxido-reductase, and pectinase. It is particularly preferred to include a xylanase as a further enzyme supplement such as a subtilisin derived from the genus Bacillus. Such xylanases are, for example, described in detail in PCT Patent Application No. WO 97/20920, which is hereby incorporated by reference.

Another aspect of the present invention is a method of treating a textile. This method involves providing a chemically modified mutant enzyme with one or more amino acid residues from an enzyme being replaced by cysteine residues, where at least some of the cysteine residues are modified by replacing thiol hydrogen in the cysteine residues with a thiol side chain. The chemically modified mutant enzyme is contacted with a textile under conditions effective to produce a textile resistant to certain enzyme-sensitive stains. Such enzyme sensitive stains include grass or blood. Preferably, the textile includes a modified enzyme. The method can be used to treat, for example, silk or wool as described in publications such as Research Disclosure 216, 034, European Patent Application No. 134,267, U.S. Pat. No. 4,533,359, and European Patent Application No. 344, 259, which are hereby incorporated by reference.

EXAMPLES

Example 1

Validation of Rapid Combinatorial Assay for the Preparation and Screening of Chemically Modified Mutant Enzymes for Amidase and Esterase Activities In a 96-well enzyme activity assay, $k_{cat}/K_M$ is obtained from the rate of product formation (v), using the limiting case of the Michaelis-Menten equation at low substrate concentration as an approximation (Equation 1, where [S] and [E] are the substrate and enzyme concentrations, respectively):

$$V \approx (k_{cat}/K_M) [S][E] \text{ for } [S] << K_M \quad \text{(Equation 1)}$$

Enzyme stock solutions were prepared in 5 mM 4-morpholineethanesulfonic acid ("MES") with 2 mM $CaCl_2$, pH 6.5 at about $5 \times 10^{-7}$ M for amidase and $5 \times 10^{-8}$ M for esterase assays. Substrate solutions were prepared in dimethyl sulfoxide ("DMSO"). The amidase substrate sucAAPF-pNa stock was 1.6 mM, which gave 0.08 mM in the well. The esterase substrate succinyl-alanine-alanine-proline-phenylalanine-thiobenzyl ester ("sucAAPF-SBn") stock solution was 1.0 mM, which gave 0.05 mM in the well. Assays were carried out in 0.1 M tris hydroxymethylaminomethane ("Tris") pH 8.6 with 0.005% Tween. Tris buffer for the esterase assay contained 0.375 nM DTNB. This buffer had to be used immediately, as the DTNB decomposed within a few hours due to the high pH of the buffer. Berglund et al., *Bioorg Med. Chem. Lett.*, 6:2507–2512 (1996) and Berglund et al., *J. Am. Chem. Soc.*, 119:5265–5266 (1997), which are hereby incorporated by reference.

A sample of each enzyme solution (~150 μL) was placed in a well in the $1^{st}$, $5^{th}$, or $9^{th}$ column of an enzyme loading plate. Rows A to G contained enzymes, and row H contained MES buffer. On a separate assay plate (Coming, flat bottom, 96-well), 10 μL of substrate solution and 180 μL of buffer were dispensed into wells along columns to be used in a run. Columns 1–4 on the assay plate contained four replicates of the enzymes in column 1 of the loading plate; columns 5–8 contained four replicates of the enzymes in column 5 of the loading plate; and columns 9–12 contained four replicates of the enzymes in column 9 of the loading plate. Reactions were initiated by transferring 10 μL of enzyme solution from the loading plate to the assay plate with an 8-channel pipette. For amidase assays, four columns were initiated for one run. For esterase assays, two columns were initiated for one run. The time delay between addition of enzyme to the first column and onset of reading was 22–30 seconds (amidase) and 10–15 seconds (esterase). Immediately after initiation, the plate was placed on a Titertech Multiscan MCC340 reader (programmed in the kinetic mode, filter 414 nm, lag time 0.0 minutes, interval 5 seconds, with automatic background subtraction of blank row H) (Labsystems, Finland) and was read for 1.0 minute (amidase) or 30 seconds (esterase). Prolonged reading, past the nearly linear part of the progress curve (up to ~50% conversion), provided an underestimate of the rate. The output from the reader represented the average rate of change in absorbance at 414 nm $min^{-1}$, measured at 5 second intervals, of the total time programmed. These data were converted to rates in $Ms^{-1}$ using $e_{414}=8581$ $M^{-1}$ $cm^{-1}$ for p-nitroanilide $e_{414}-8708^{-M}$ $cm^{-1}$ for 3-carboxylate-4-nitrothiophenolate. Both extinction coefficients were determined on the reader using the same conditions and background subtraction as in the assay. The path length was 5 mm. The rates were corrected for active enzyme concentration, and the four replicates for each enzyme were averaged.

TABLE 1

$k_{cat}/K_M$ obtained for amidase activity at pH 8.6[a]

| Enzyme | Type of Assay | $k_{cat}/K_M$ ($s^{-1}mM^{-1}$) |
|---|---|---|
| WT | cuvette[b] (standard[c]) | 76 ± 7[f] |
| WT | Cuvette (low substrate[d]) | 75 |
| WT | 96-well[e] (low substrate) | 75 ± 5[f] |
| WT | 96-well (standard) | 80 ± 17[c] |
| L217C-SCH$_2$C$_6$H$_5$ | 96-well (low substrate) | 52 ± 6[f] |
| L217C-S CH$_2$C$_6$H$_5$ | 96-well (standard) | 48 ± 3[c] |
| L217C-S(CH$_2$)$_5$CH$_3$ | 96-well (low substrate) | 113 ± 18[f] |
| L217C-S(CH$_2$)$_5$CH$_3$ | 96-well (standard) | 97 ± 12[c] |

[a] All assays were done at room temperature (ca. 20° C.). For assays in 1 mL curvettes, the cell holder was thermostatted to 20° C.
[b] Kinetic assay in 1 mL cuvettes.
[c] Complete enzyme kinetics by the method of initial rates, where $k_{cat}/K_M$ was obtained from $k_{cat}$ and $K_M$ values and the errors were obtained from the curve-fitting error in $k_{cat}$ and $K_M$.
[d] Measurement of $k_{cat}$ and $K_M$ using the low substrate approximation (see text).
[e] Assay performed on microtiter plates instead of cuvettes.
[f] Mean ± standard error of 4 replicates.

The value of $k_{cat}/K_M$ (amidase) obtained using the 96-well assay (Table 1) was the same as value obtained by the method of initial rates in 1 mL cuvettes at room temperature. The $k_{cat}/K_M$ (amidase) values obtained for WT and CMMs at 25° C. were 2 times higher than the values obtained at room temperature. Normally, the cuvette assay is performed at 25° C. The $k_{cat}/K_M$ value obtained in the cuvette at 20° C. using a complete kinetic evaluation and the value calculated from the rate at the lowest substrate concentration (Equation 1) were the same, indicating that the low substrate approximation held for WT (Table 1).

To farther validate the method, complete kinetic experiments were performed on 96-well plates by running 8 different substrate concentrations along the rows and one enzyme/column. Values of $k_{cat}/K_M$ obtained from these experiments were the same as values obtained with the low substrate approximation for WT and two L217CCMMs, indicating that the low substrate approximation also held for CMMs. Similarly, $k_{cat}/K_M$ values for esterase obtained on the plate did not differ significantly from values obtained with the standard assay (Table 2).

TABLE 2

$k_{cat}/K_M$ obtained for esterase activity at pH 8.6[a]

| Enzyme | Type of Assay | $k_{cat}/K_M$ (s$^{-1}$mM$^{-1}$) |
|---|---|---|
| WT | 96-well (low substrate) | 3321 ± 256 |
| L217C | Cuvette (standard) | 5540 ± 798 |
| L217C | 96-well (low substrate) | 5563 ± 419 |
| N62C | Cuvette (standard) | 4380 ± 655 |
| N62C | 96-well (low substrate) | 4151 ± 198 |
| N62C-SCH$_3$ | Cuvette (standard) | 10100 ± 1287 |
| N62C-SCH$_3$ | 96-well (low substrate | 8739 ± 765 |

[a]Notation as in Table 1.

In the esterase assay, temperature did not have a significant effect.

The reactions were left at room temperature and were tested for free thiol groups after 2 hours as follows. On a separate plate, 10 μL of reaction mixture was added to 60 μL of DTNB-containing Tris buffer (pH 8.6) and the monitoring plate was scanned at 414 mn 15 minutes later. No difference between the WT and the modified cysteine mutants were detected, indicating that the reaction was complete. To quench the reaction, 10 μL of MES, at a pH of 6.5 was added to each well, and 20 μL of the mixture from each well was diluted with 980 μL of MES buffer (in Eppendorf tubes). An amidase loading plate was prepared with the diluted mixtures; an esterase loading plate was prepared with 10 μL of diluted mixture and 90 μL of MES buffer in the appropriate wells. From this point on, the assays were the same as described in Example 1. Each reaction replicate was assayed in duplicate. The $k_{cat/KM}$ values were calculated according to Equation 1, basing [E] on the concentration of active enzyme in the parent mutant and assuming no significant denaturation. Since little difference was observed between the two reaction replicates, the 4 values for each combination were averaged in the final results.

The amidase $k_{cat}/K_M$ value for N62C-a and S166C-a obtained in the screen was about 2 times lower than the value obtained for the fully characterized enzymes (Table 3), consistent with the previous assay validation results in Example 1.

TABLE 3

Comparison of data from the screen and the corresponding fully characterized enzymes.

| Enzyme | Reagent | Amidase $k_{cat}/K_M$ (s$^{-1}$ mM$^{-1}$)[a] Screen | Amidas $k_{cat}/K_M$ (s$^{-1}$ Mm-)[b] Fully characterized | Esterase $k_{cat}/K_M$ (s$^{-1}$ mM$^{-1}$)[1] Screen | Amidas $k_{cat}/K_M$ (s$^{-1}$ mM$^{-1}$)[2] Fully characterized |
|---|---|---|---|---|---|
| WT | | 121 ± 3 | 178 ± 15 | 3890 ± 170 | 3560 ± 540 |
| N62C | 1a | 207 ± 13 | 379 ± 35 | 6510 ± 560 | 6330 ± 1360 |
| | 1c | 86 ± 6 | 93 ± 4 | 5680 ± 1000 | 7870 ± 160 |
| | 1d | 74 ± 11 | 442 ± 36 | 7680 ± 1410 | 50700 ± 2160 |
| | 1e | 111 ± 3 | 198 ± 44 | 7520 ± 710 | 14260 ± 590 |
| S166C | 1a | 10 ± 1 | 20 ± 1 | 1160 ± 140 | 4920 ± 1320 |
| | 1c | 17 ± 1 | 68 ± 2 | 1746 ± 120 | 5798 ± 106 |
| | 1d | 16 ± 1 | 72 ± 3 | 2370 ± 91 | 11460 ± 400 |
| | 1e | 14 ± 0 | 67 ± 3 | 784 ± 75 | 5198 ± 145 |

[a]Mean ± standard error from 4 replicates, obtained at room temperature (see text).
[b]Values and error calculated from individual $k_{cat}$ and $K_M$ values obtained t 25° C.

Example 2

Figure 1:
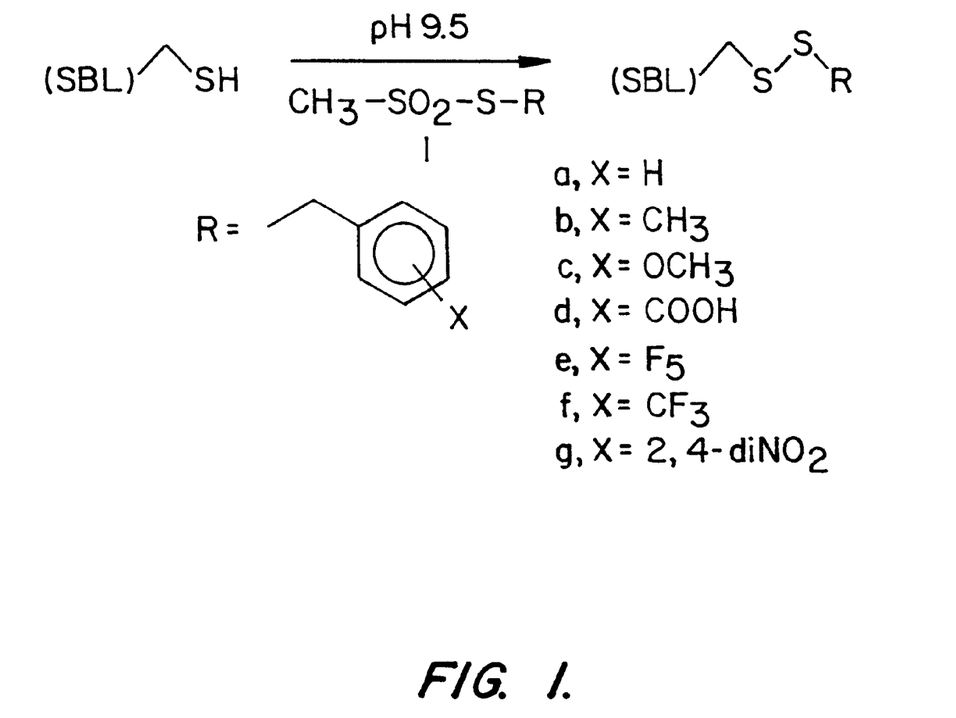
FIG. 1 shows the chemical modification of cysteine mutants of subtilisin Bacillus lentus ("SBL") to generate chemically modified mutant enzymes.
Figure 2:
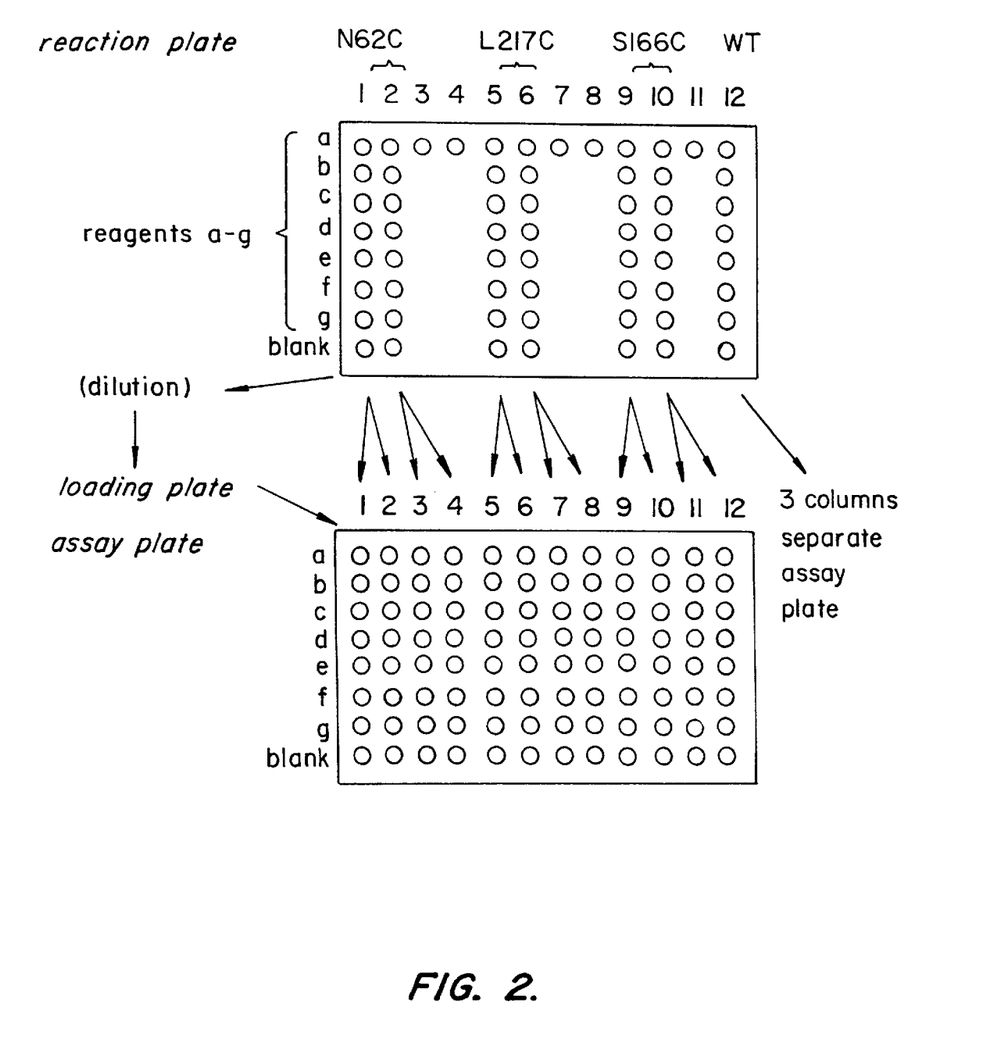
FIG. 2 shows a 96-well colorimetric assay in accordance with the present invention.

Generation of an Array of New CMMs on a 96-well plate and Screening of the New CMMs for Amidase and Esterase Activity Using the Rapid Combinatorial Assay for the Preparation and Screening of Chemically Modified Mutant Enzymes for Amidase and Esterase Activities For the small-scale preparation of new CMMs, combinations of 7 different aromatic methanethiosulfonate ("MTS") reagents (1 a–g) (FIG. 1) and 3 cysteine mutants (N62C, L217C and S166C), as well as a WT control were set up on a 96-well plate as shown in the top part of FIG. 2. Two replicates of each mutant were prepared with each reagent. One reagent, benzyl MTS (1a), had already been evaluated in large scale modifications, and was included for comparative purposes. The reaction mixture in each well consisted of 20 μL of enzyme solution (in 5 mM MES, 2 mM CaCl$_2$, pH 6.5, ca, 8×10$^5$ M), 40 μL of 2[N-cyclohexylamino] ethanesulfonic acid ("CHES") buffer (70 mM CHES, 5 mM MES, 2 mM CaCl$_2$, pH 9.5) and 10 μL of MTS reagent in acetonitrile (ca. 1×10$^2$ M). The blanks on the reaction plate were 20 μL of MES, 40 μL of CHES and 10 μL of acetonitrile.

Figure 3:
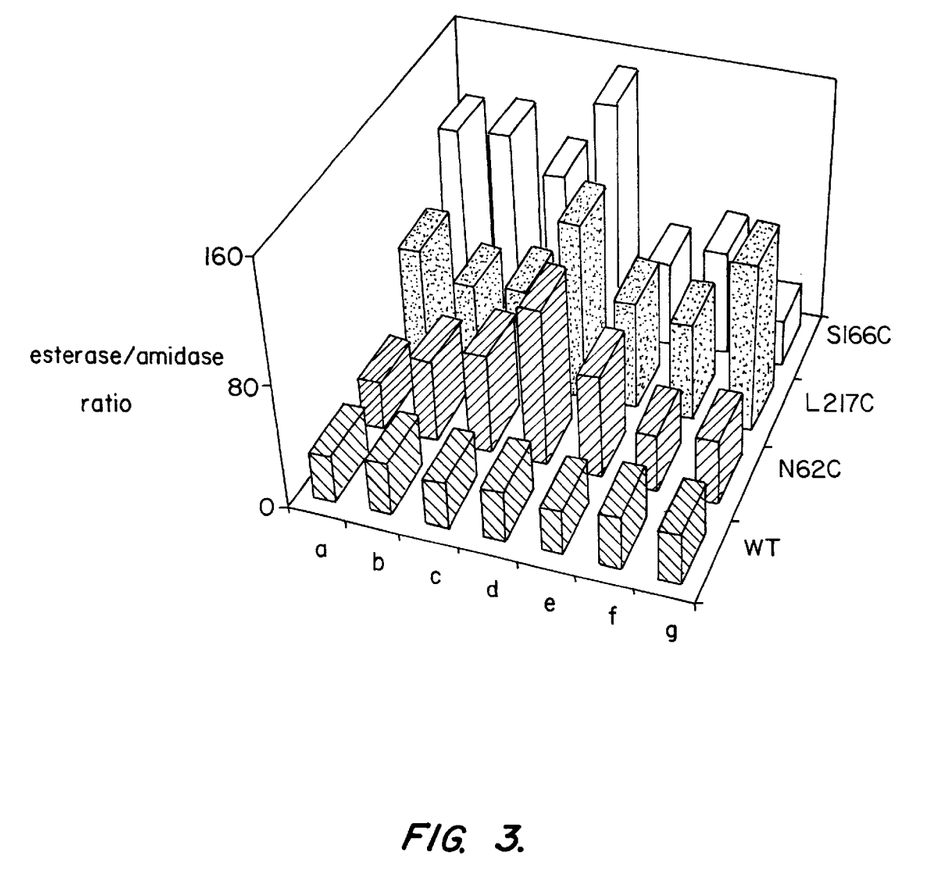
FIG. 3 is a three-dimensional plot of $[k_{cat}/K_M$ esterase]/$[k_{cat}/K_M$ amidase] v. a–g thiol side chain v. chemically modified mutant, showing the results obtained for the ratio of $k_{cat}/K_M$ for esterase/amidase activity. The reagents are set forth in FIG. 1.

The factor by which amidase $k_{cat}/K_M$ values for N62C-a and S166C-a differed from WT was the same for the screen and the characterized CMMs, indicating that the screen was giving the correct relative pattern for amidase activity. With respect to esterase, the $k_{cat}/K_M$ values for WT and N62C-a were the same in the screen and the characterized enzyme (Table 3), consistent with validation results. For S166C-a, however, the screen underestimated the esterase $k_{cat}/K_M$ value ~5-fold. Given that the amidase value for S166C-a was not underestimated, the reason for the discrepancy could not be significant denaturation. The seven WT control treatments had the same esterase and amidase activity (and hence esterase/amidase ratio, FIG. 3), indicating that the reagents themselves did not cause differential denaturation.

Figure 4:
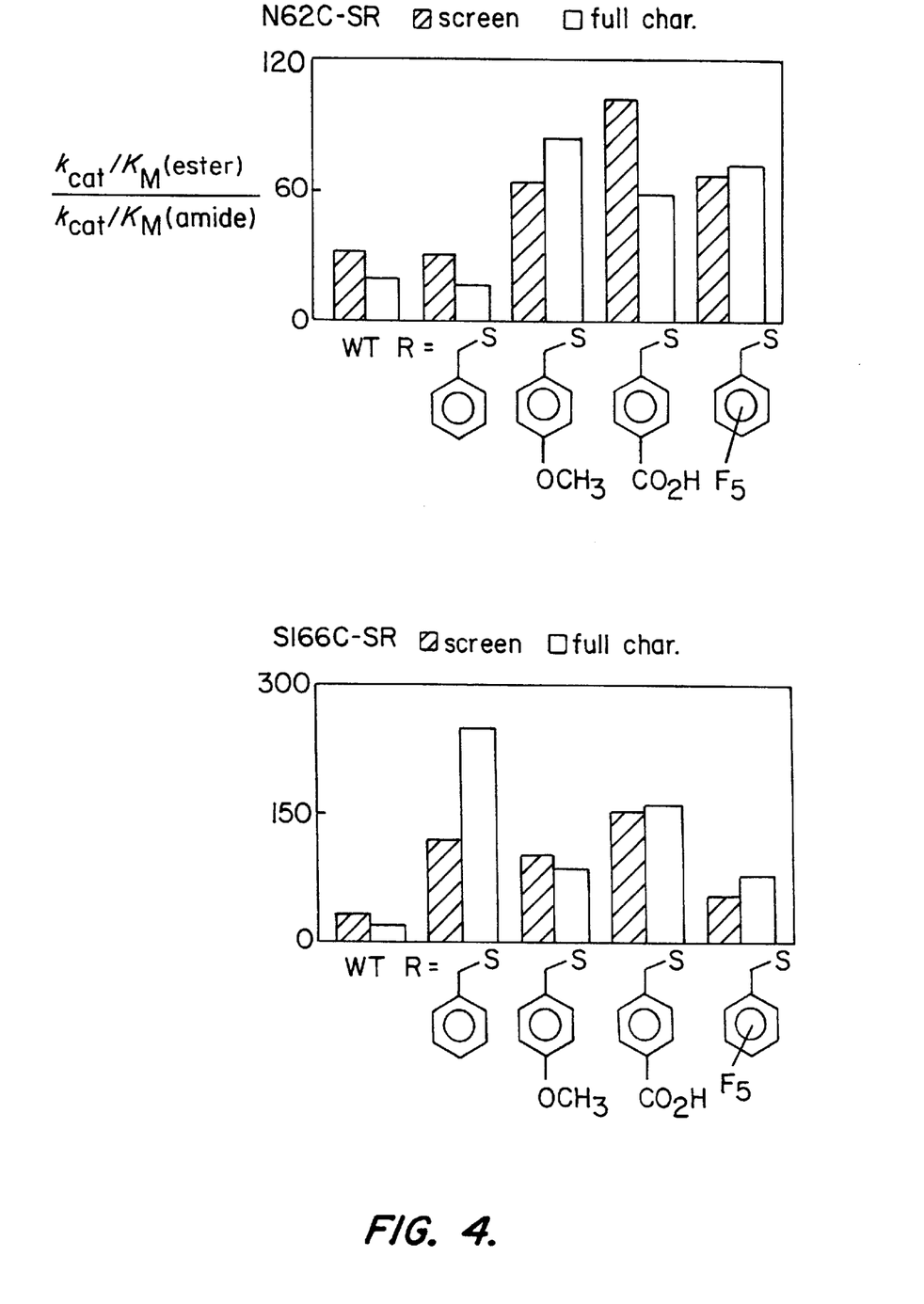
FIG. 4 shows a comparison of the esterase/amidase specificity ratio from the rapid combinatorial assay of the present invention and the corresponding fully characterized enzymes.

The screen results (FIG. 4) suggested that N62c–d and e had greatly improved esterase activity as compared to WT. In the 166 family, some CMMs appeared to have very favourable esterase/amidase ratios. Members of the 217 family were intermediate with respect to esterase and esterase/amidase ratio. To determine the reliability of these results, N62C- and S166C-c, d, and e were prepared and characterized. The $k_{cat}/K_M$ values from the screen and the characterized enzymes agreed within limits of error discussed above, except for both 4-carboxybenzyl (d) CMMs for which amidase and esterase were both ~5-fold underestimated in the screen (Table 3), because significant denaturation had occurred in both CMMs. The concentration of active enzyme was 4-fold lower than expected from the parent mutant. In spite of this problem, the screen clearly showed that both 4-carboxybenzyl (d) CMMs had improved esterase activity relative to the S-benzyl (a) variants (Table 3). Furthermore, the screen correctly predicted significantly improved esterase/amidase specificity ratios for N62C- and S1266C-c, d and e (FIG. 4).

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A chemically modified mutant *Bacillus lentus* subtilisin enzyme with one or more amino acid residues from the enzyme being replaced by cysteine residues, wherein at least some of the cysteine residues are modified by replacing the thiol hydrogen in the cysteine residue with a thiol side chain, wherein the thiol side chain is selected from the group consisting of $-SCH_2(p-CH_3-C_3-C_6H_4)$, $-SCH_2(p-OCH_3-C_6H_4)$, $-SCH_2(p-CF_3-C_6H_4)$, and $-SCH_2(2,4-diNO_2-C_6H_3)$ and wherein the modified enzyme is a subtilisin.

2. A chemically modified mutant enzyme according to claim 1, wherein the amino acid replaced by a cysteine is an amino acid selected from the group consisting of asparagine, leucine and serine.

3. A chemically modified mutant enzyme according to claim 1, wherein the amino acid replaced with a cysteine is in a subsite of the enzyme.

4. A chemically modified mutant enzyme according to claim 3, wherein the subsite is selected from the group consisting of $S_1$, $S_1'$, and $S_2$.

5. A chemically modified mutant enzyme according to claim 1, wherein the thiol side chain is $-SCH_2(p-CH_3-C_6H_4)$.

6. A chemically modified mutant enzyme according to claim 1, wherein the thiol side chain is $-SCH_2(p-OCH_3-C_6H_4)$.

7. A chemically modified mutant enzyme according to claim 1, wherein the thiol side chain is $-SCH_2(p-CF_3-C_6H_4)$.

8. A chemically modified mutant enzyme according to claim 1, wherein the thiol side chain is $-SCH_2(2,4-diNO_2-C_6H_3)$.

9. A detergent additive comprising the chemically modified mutant enzyme of claim 1.

10. A feed additive comprising the chemically modified mutant enzyme of claim 1.

* * * * *

UNITED STATES PATENT AND TRADEMARK OFFICE
CERTIFICATE OF CORRECTION

PATENT NO. : 6,284,512 B1
DATED : September 4, 2001
INVENTOR(S) : Jones et al.

It is certified that error appears in the above-identified patent and that said Letters Patent is hereby corrected as shown below:

Column 11,
Line 24, delete "-$SCH_2(p\text{-}CH_3\text{-}C_3\text{-}C_6H_4)$," and insert -- -$SCH_2(p\text{-}CH_3\text{-}C_6H_4)$, --

Signed and Sealed this

Second Day of July, 2002

Attest:

Attesting Officer

JAMES E. ROGAN
*Director of the United States Patent and Trademark Office*